(12) United States Patent
Busujima et al.

(10) Patent No.: US 8,563,300 B2
(45) Date of Patent: Oct. 22, 2013

(54) INCUBATOR

(75) Inventors: Hiroki Busujima, Ota (JP); Yoshihiro Takahashi, Gunma-ken (JP)

(73) Assignee: Panasonic Healthcare Co., Ltd., Ehime (JP)

( * ) Notice: Subject to any disclaimer, the term of this patent is extended or adjusted under 35 U.S.C. 154(b) by 101 days.

(21) Appl. No.: 13/241,619

(22) Filed: Sep. 23, 2011

(65) Prior Publication Data

US 2012/0083030 A1    Apr. 5, 2012

(30) Foreign Application Priority Data

Sep. 30, 2010   (JP) ................................. 2010-222369

(51) Int. Cl.
*C12M 1/00* (2006.01)
*C12M 3/00* (2006.01)
*A61L 2/00* (2006.01)
*B06B 1/00* (2006.01)

(52) U.S. Cl.
USPC .............. 435/303.1; 422/1; 422/20; 422/128; 435/283.1; 435/289.1; 435/305.1

(58) Field of Classification Search
USPC ................... 435/283.1–309.4; 422/1, 20, 128
See application file for complete search history.

(56) References Cited

U.S. PATENT DOCUMENTS

2002/0047311 A1* 4/2002 Hugh ............................ 307/116
2010/0173401 A1* 7/2010 Kobayashi et al. ........ 435/303.1

FOREIGN PATENT DOCUMENTS

JP    2010-154793 A    7/2010
JP    2010154792 A     7/2010

OTHER PUBLICATIONS

English translation for Japanese Publication No. 2010-154793 Published Jul. 15, 2010 (11 pages).
English translation for Japanese Publication No. 2010-154792 Published Jul. 15, 2010 (11 pages).

* cited by examiner

*Primary Examiner* — Nathan Bowers
*Assistant Examiner* — Lydia Edwards
(74) *Attorney, Agent, or Firm* — McDermott Will & Emery LLP

(57) ABSTRACT

An incubator comprising: a culture chamber configured to accommodate culture; a dish structure configured to contain a liquid; an ultrasonic vibrator provided in a part of the dish structure, the ultrasonic vibrator configured to atomize the liquid; and a gas-liquid contact structure configured to bring the atomized liquid into contact with air in the chamber to be cultured.

7 Claims, 12 Drawing Sheets

INCUBATOR

CROSS-REFERENCE TO RELATED APPLICATION

This application claims the benefit of priority to Japanese Patent Application No. 2010-222369, filed Sep. 30, 2010, of which full contents are incorporated herein by reference.

BACKGROUND OF THE INVENTION

1. Field of the Invention

The present invention relates to an incubator, and particularly relates to a technology to enable environment control and sterilization control to be performed efficiently for an inside of a culture chamber.

2. Description of the Related Art

A carbon dioxide ($CO_2$) incubator (hereinafter referred to as "incubator") is known, which includes a means to supply a $CO_2$ gas into a chamber containing culture and a sensor to detect density of the $CO_2$ gas inside a culture chamber (chamber), and controls a supply amount of the $CO_2$ gas according to the density of the $CO_2$ gas.

In the case of changing culture after cultivation thereof using such an incubator, since the culture itself such as a cell and a microorganism, or a bacterium, a virus, etc., which are parasitic on the culture, adhere to an inner wall of the chamber or float in the chamber, it is necessary to perform sterilization processing for the inside of the chamber so as to avoid contamination of next culture caused by such matters.

With respect to a mechanism to sterilize the inside of the chamber, for example, Patent Document 1 (Japanese Laid-Open Patent Publication No. 2010-154792) discloses the $CO_2$ incubator including: a fan; an ozone generator; an ozone sensor that measures ozone density in a bypass provided long with the chamber; a bypass heater, provided separately from the heater, to heat the inside of the chamber; a first temperature sensor to measure a temperature inside the chamber; a second temperature sensor to measure a temperature in the bypass; a control unit; a water dish to enhance humidity control of air inside the chamber and sterilizing function of ozone gas; etc.

Further, Patent Document 2 (Japanese Laid-Open Patent Publication No. 2010-154793) discloses a $CO_2$ incubator including: a chamber to accommodate culture and a door to block an opening of the chamber, which can freely be opened or closed; a valve to take $CO_2$ gas supplied from the outside into the chamber; a fan to circulate air inside the chamber; an ultraviolet lamp to emit ultraviolet rays, etc., and describes that it is provided with a sterilizing gas generating device in the chamber that generate gas having a sterilizing effect (hydrogen peroxide gas, ozone gas) when sterilization processing is performed for an inside of the chamber.

In order to properly maintain the humidity of the air inside the chamber using the water dish as described in Patent Document 1, it is necessary to perform control so that a proper amount of water is retained in the water dish. Thus, a user of the incubator is required to access the water dish disposed on the bottom face of the incubator to monitor the remaining amount of the water periodically. To properly control the humidity throughout the inside of the chamber, it is necessary to efficiently evaporate the water in the water dish to be spread throughout the inside of the chamber.

In Patent Document 2, the sterilization within the chamber is performed using the sterilizing gas generating device, the sterilizing gas generating device needs to be brought into the chamber, which causes the user to take trouble every time the sterilization processing is performed.

The present invention has been conceived in light of such problems and an object thereof is to provide an incubator capable of efficiently performing environment control and sterilization control inside a culture chamber.

SUMMARY OF THE INVENTION

An incubator according to an aspect of the present invention, includes: a culture chamber configured to accommodate culture; a dish structure configured to contain a liquid; an ultrasonic vibrator provided in a part of the dish structure, the ultrasonic vibrator configured to atomize the liquid; and a gas-liquid contact structure configured to bring the atomized liquid into contact with air in the chamber to be cultured.

Other features of the present invention will become apparent from descriptions of this specification and of the accompanying drawings.

BRIEF DESCRIPTION OF THE DRAWINGS

For more thorough understanding of the present invention and advantages thereof, the following description should be read in conjunction with the accompanying drawings, in which.

DETAILED DESCRIPTION OF THE INVENTION

At least the following details will become apparent from descriptions of this specification and of the accompanying drawings.

First Embodiment

FIGS. 1 to 4 depict an incubator 1 which is to be described as a first embodiment of the present invention. In the following description, a coordinate system is to be set in directions indicated in these drawings.

Figure 1:
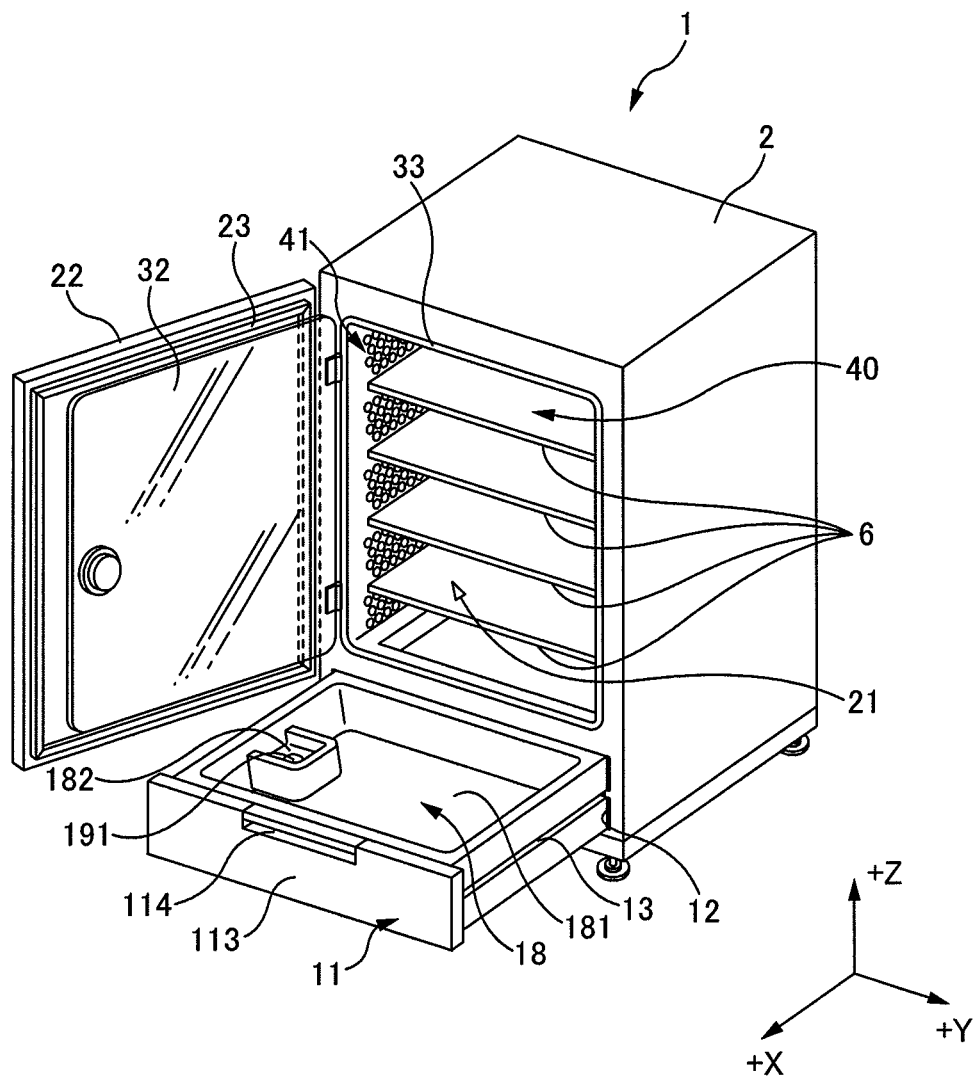
FIG. 1 is an external perspective view of an incubator 1 which is to be described as a first embodiment of the present invention as viewed from a front (+X direction)
Figure 2:
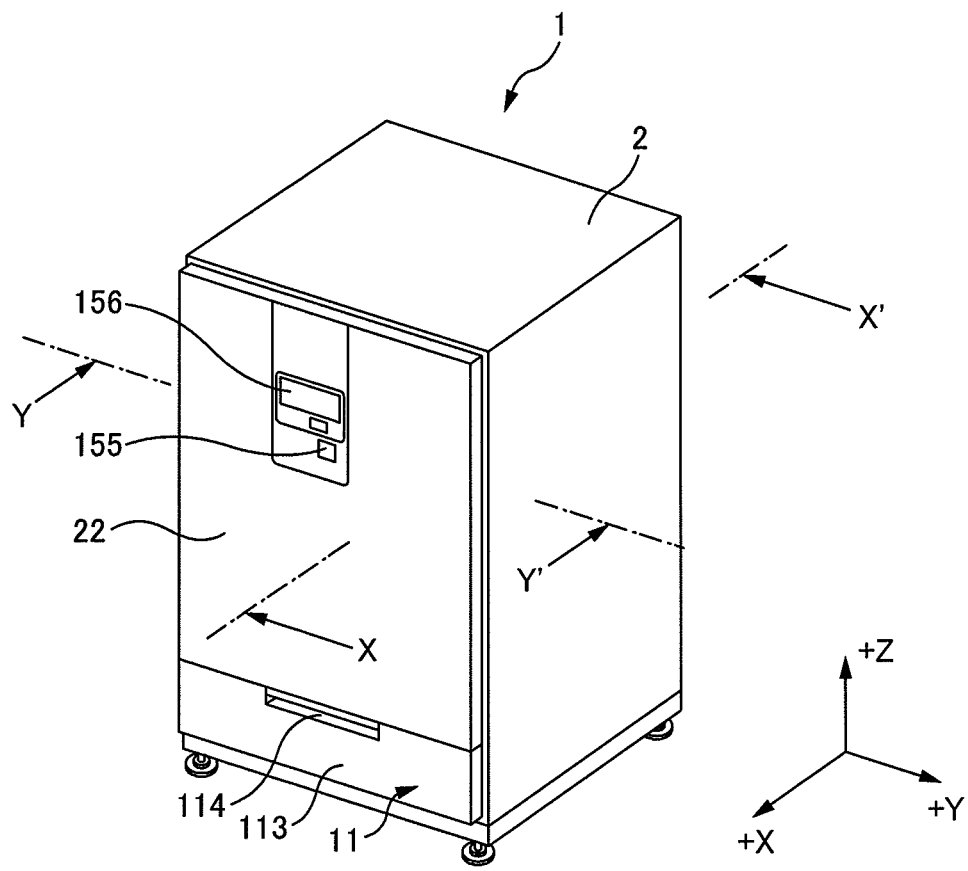
FIG. 2 is an external perspective view of an incubator 1 which is to be described as a first embodiment of the present invention as viewed from a front (+X direction)
Figure 3:
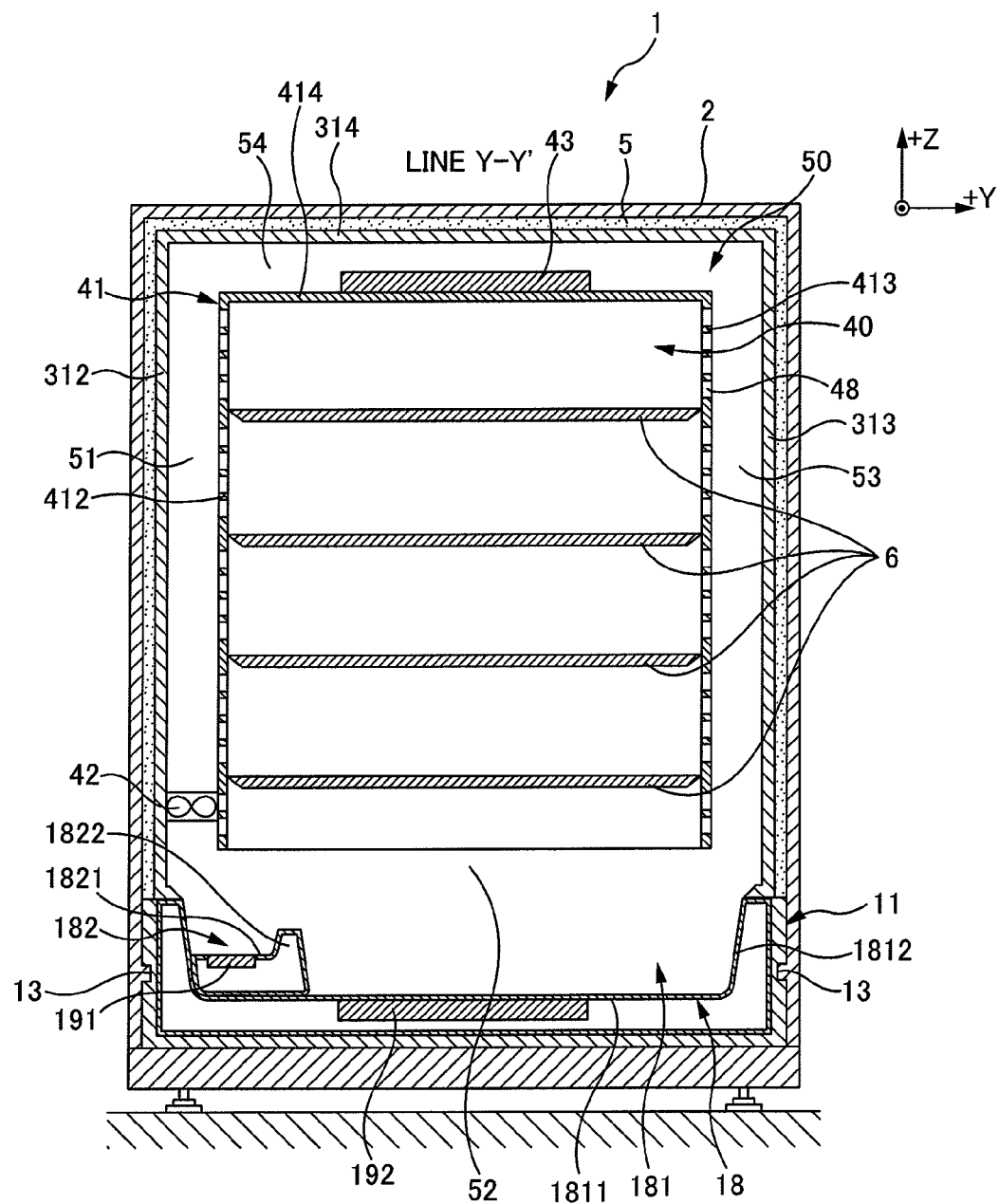
FIG. 3 is a cross-sectional view of an incubator 1 which is to be described as a first embodiment of the present invention along a line Y-Y' of FIG. 2.
Figure 4:
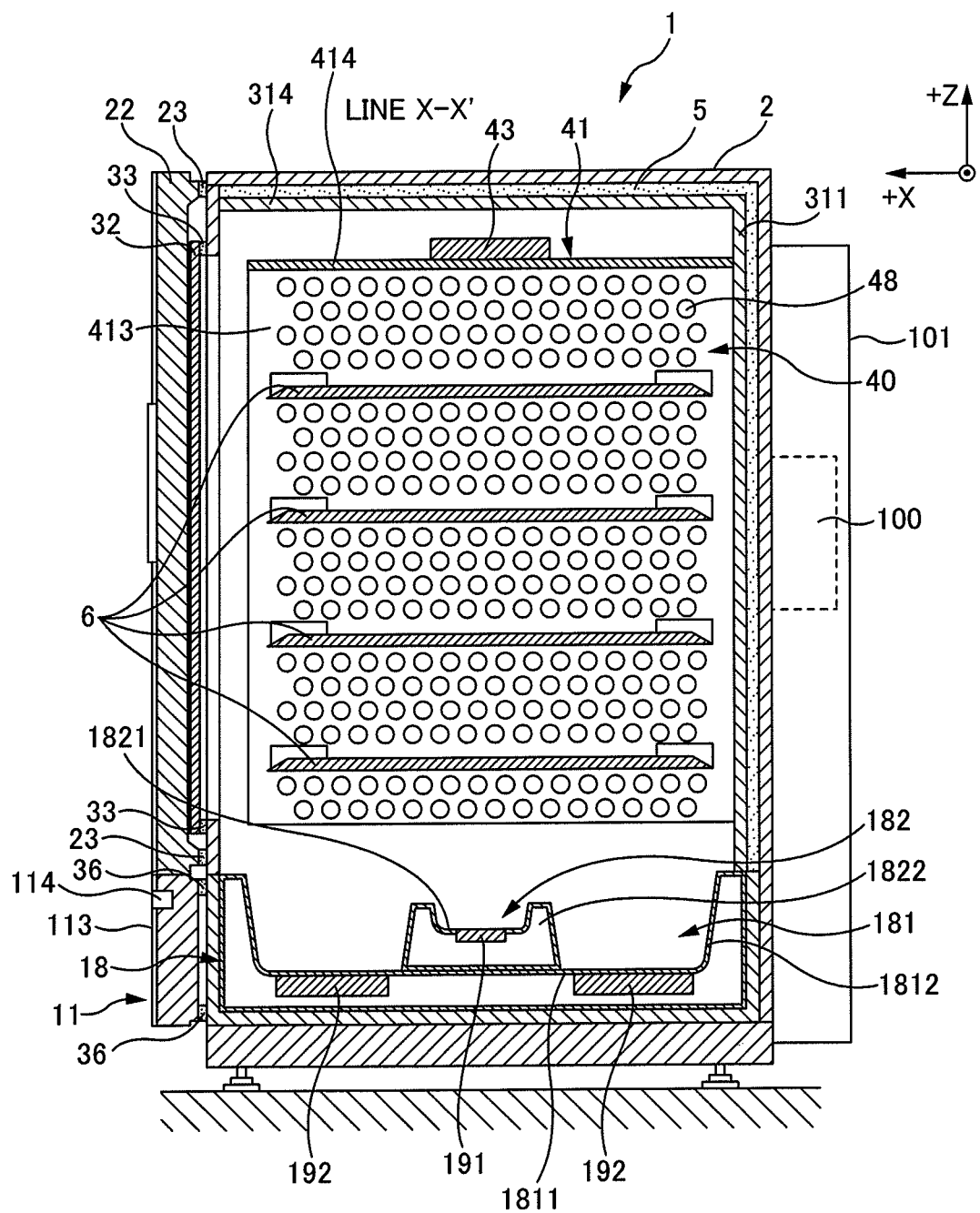
FIG. 4 is a cross-sectional view of an incubator 1 which is to be described as a first embodiment of the present invention along a line X-X' of FIG. 2.

FIG. 1 is an external perspective view of an incubator 1 as viewed from the front (+X direction). FIG. 2 is an external perspective view of the incubator 1 as viewed from the same direction as in FIG. 1, and depicts the incubator 1 in a state where an outer door 22 and an inner door 32, which will be described later, are closed and a drawer 11, which will be described later, is stored in a storage unit 12, which will be described later, provided in an outer box 2. FIG. 3 is a cross-sectional view of the incubator 1 along a line Y-Y' of FIG. 2. FIG. 4 is a cross-sectional view of the incubator 1 along a line X-X' of FIG. 2.

As illustrated in these drawings, the incubator 1 includes the outer box 2, an inner box 3 provided inside the outer box 2, and a drawer structure (drawer 11 and storage unit 12) provided below (−Z direction) the inner box 3.

The outer box 2 is a box substantially of a rectangular parallelepiped shape, which is made of a material such as stainless steel. The inner box 3 is a box substantially of a rectangular parallelepiped shape, which is slightly smaller than an external form of the outer box 2 and is made of a material such as stainless steel. As illustrated in FIGS. 3 and 4, the inner box 3 includes a backboard 311, two sideboards 312 and 313 opposed to each other, and a ceiling board 314. A structure to support the inner box 3 in the incubator 1 is omitted from the drawings.

A heat insulating material 5 is filled between the outer box 2 and the inner box 3. An opening 21 is formed on a side face on the +X side of the outer box 2, and two doors (outer door 22 and inner door 32) to block this opening 21 to keep air-tightness inside the incubator 1 are mounted on the outer box 2 by way of hinges, etc. The outer door 22 and the inner door 32 can adopt a structure (reversible structure) capable of opening and closing whether a pivot is positioned on the right side or on the left side thereof.

The outer door 22 is made of a material such as stainless steel, is substantially of a rectangular shape slightly greater in external form than the inner door 32, and has the heat insulating material filled in the inside. Along the inner periphery of the outer door 22, packing 23 is provided to ensure the air-tightness in the incubator 1. The inner door 32 is a board made of a transparent material such as resin and glass substantially in a rectangular shape. In such a part of the periphery of the opening 21 of the outer box 2 that abuts on the inner door 32, packing 33 is provided to ensure the air-tightness inside the incubator 1.

In an internal space (chamber) of the inner box 3, a plurality of shelf boards 6 are provided to place culture such as cells and microorganisms. Around the shelf boards 6, a case 41 is provided that is configured including a backboard 411 disposed at the back (−X side) of the shelf boards 6, two sideboards 412 and 413 disposed on both sides (±Y direction) of the shelf boards 6, and a ceiling board 414 disposed over (+Z direction) the shelf boards 6. The case 41 is made of a material such as stainless steel.

On the faces of the sideboards 412 and 413, a large number of air holes 48 are formed by a punching process, etc. In the following description, the space inside the case 41 will be referred to as a culture chamber 40. A structure to support the case 41 in the incubator 1 is omitted from the drawings.

The drawer 11 is a box substantially of a rectangular parallelepiped shape, which is made of a material such as stainless steel and resin. On both side faces 111 and 112 of the drawer 11 (and in corresponding positions of the storage unit 12), a rail structure 13 is provided to support the drawer 11 so as to be able to be pulled out or be pushed in smoothly with respect to the storage unit 12.

On the front side (+X side) of a front panel 113 of the drawer 11, a handle 114 is provided that serves as a handling part when the user pulls out or pushes in the drawer 11. Along the periphery of the inner side (−X side) of the front panel 113 of the drawer 11, packing 36 is provided to ensure air-tightness inside the incubator 1.

As illustrated in FIG. 3, a first clearance space 51 is formed between the sideboard 412 of the case 41 and the sideboard 312 of the inner box 3. A second clearance space 52 connected to the first clearance space 51 is formed between the case 41 (lowermost shelf board 6 of the case 41) and the drawer 11. A third clearance space 53 connected to the second clearance space 52 is formed between the sideboard 413 of the case 41 and the sideboard 313 of the inner box 3. Further, a fourth clearance space 54 connected to the third clearance space 53 and the first clearance space 51 is formed between the ceiling board 414 and the ceiling board 314 of the inner box 3 described above. Around the shelf boards 6, a duct 50 through which an air circulating in the inner box 3 flows is formed by the first to the fourth clearance spaces 51 to 54.

As illustrated in the drawing, a fan 42 (fan motor, multiblade fan, etc.) is provided in a flow path of the duct 50 (in the first clearance space 51 in the same drawing). When performing a cultivation operation using the incubator 1 or the sterilization processing for the inside of the incubator 1, the rotation of the fan 42 generates an air flow circulating in the duct 50 or in the culture chamber 40. On the top face side of the ceiling board 414 in the duct 50, a heater 43 to heat the air flowing through the duct 50 is provided.

As illustrated in FIG. 3 or 4, a dish structure 18 is provided inside the drawer 11. The dish structure 18 includes a first containing unit 181 demarcated by a first bottom face 1811 and a first side face 1812 set up around the first bottom face 1811. The dish structure 18 also includes a second containing unit 182 provided in the first containing unit 181 and demarcated by a second bottom face 1821, raised up by a predetermined height from the first bottom face 1811 of the first containing unit 181, and a second side face 1822, set up around the second bottom face 1821 and having a height shorter than that of the first side face 1811.

The first bottom face 1811 of the first containing unit 181 is provided with a heater 192 to heat a liquid contained in the dish structure 18. The second bottom face 1821 of the second containing unit 182 is provided with an ultrasonic vibrator 191.

In addition to the above configuration, the incubator 1 includes a control device 100 to perform an operation control, state monitoring, etc., of the incubator 1. As illustrated in FIG. 4, the control device 100 is accommodated in a cover 101 disposed on the back side of the outer box 2, the outer door 22, etc., for example.

Figure 5:
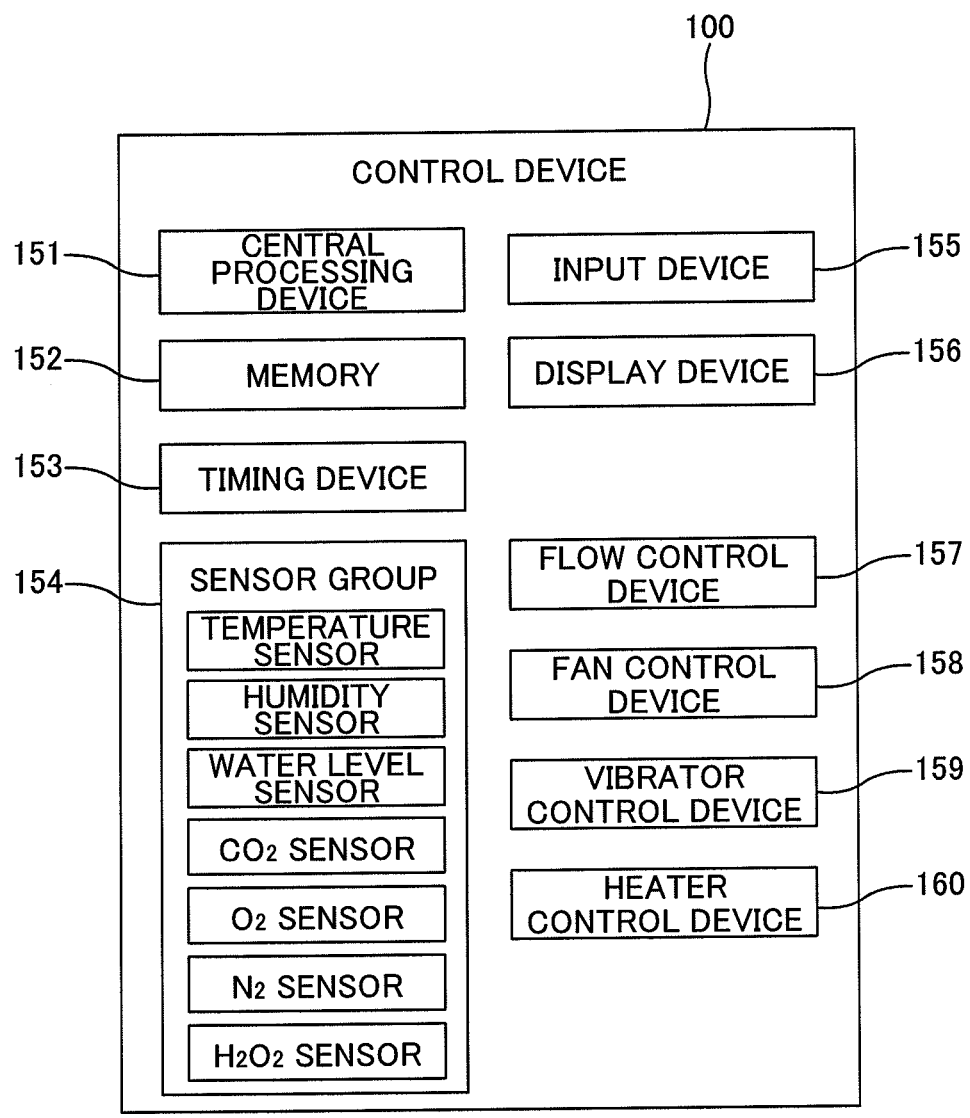
FIG. 5 is a block diagram of a control device 100.

FIG. 5 is a block diagram of the control device 100. As illustrated in the drawing, the control device 100 includes a central processing device 151, a memory 152, a timing device 153, an input device 154, a display device 155, a sensor group 156, a flow control device 157, a fan control device 158, a vibrator control device 159, and a heater control device 160.

The central processing device 151 is configured using a CPU (Central Processing Unit), an MPU (Microprocessor Unit), etc. The central processing device 151 has a function of performing overall control of the control device 100.

The memory 152 is a volatile or non-volatile memory device that stores programs to be read and executed by the central processing device 151 and data to be referred to by the central processing device 151.

The timing device 153 generates time-related data such as date and time information and elapsed time information. The information generated by the timing device 153 is used for a function of drive control based on the timing information, which the flow control device 157, the fan control device 158, the vibrator control device 159, and the heater control device 160 have, for example.

The input device 154 is a user interface that accepts, from the user, input information such as information to set the operation of the incubator 1, and is a keyboard, a touch panel, etc, for example. The central processing device 151 controls the flow control device 157, the fan control device 158, the vibrator control device 159, and the heater control device 160, based on the information accepted by the input device 154.

The display device 155 is a user interface that provides the user with an operational status, monitoring information, etc., of the incubator 1 as visual information, and is a liquid crystal display, an organic EL panel, etc., for example. The central processing device 151 acquires the operational status and the monitoring information from the flow control device 157, the fan control device 158, the vibrator control device 159, and the heater control device 160, and outputs the acquired information to the display device 155.

The sensor group 116 includes a temperature sensor to measure a temperature inside the inner box 3, a humidity sensor to measure a humidity inside the inner box 3, a water level sensor to detect a level of the liquid retained in the first containing unit 181 and the second containing unit 182, and a carbon dioxide (hereinafter referred to as $CO_2$) sensor to measure a density of $CO_2$ inside the inner box 3. The group may further include an oxygen (hereinafter referred to as $O_2$) sensor to measure a density of $O_2$ inside the inner box 3, a nitrogen (hereinafter referred to as $N_2$) sensor to measure a density of $N_2$ inside the inner box 3, a hydrogen peroxide (hereinafter described as $H_2O_2$) sensor to measure a density of $H_2O_2$ inside the inner box 3, etc.

The flow control device 157 controls (PID (Proportional Integral Derivative) control, etc.) a solenoid valve (not shown) provided in a pathway of a gas supply tube (not shown), having one end thereof provided to run through from the outside of the outer box 2 into the inner box 3 and having the other end thereof connected to a gas supply source such as a gas bomb; and controls the supply of gas 8 ($CO_2$, $O_2$, etc.) from a nozzle into the inner box 3. Based on the information acquired from the sensor group 116, the central processing device 151 controls the flow control device 157 so that a gas density ($CO_2$ density, $O_2$ density, etc.) inside the culture chamber 40 becomes appropriate.

The fan control device 158 controls (PID control, etc.) the number of rotations of the fan 42. Based on the information acquired from the sensor group 116, the central processing device 151 controls the fan control device 158 so that the speed of the air flowing through the duct 50 becomes appropriate.

The vibrator control device 159 controls (PID control, etc.) an operation (on/off, frequency, etc.) of the ultrasonic vibrator 191. Based on the information acquired from the sensor group 116, the central processing device 151 controls the vibrator control device 159 so that the humidity and the density of $H_2O_2$ inside the culture chamber 40 become appropriate.

The heater control device 160 controls (PID control, thermistor control, etc.) operations (on/off, temperature, etc.) of the heater 43 and the heater 192. Based on the information acquired from the sensor group 116, the central processing device 151 controls the heater control device 160 so that the temperature of the liquid retained in the dish structure 18, the humidity inside the culture chamber 40, the temperature of the air flowing through the duct 50, etc., become appropriate.

<Operation when Humidification is Performed>

Figure 6:
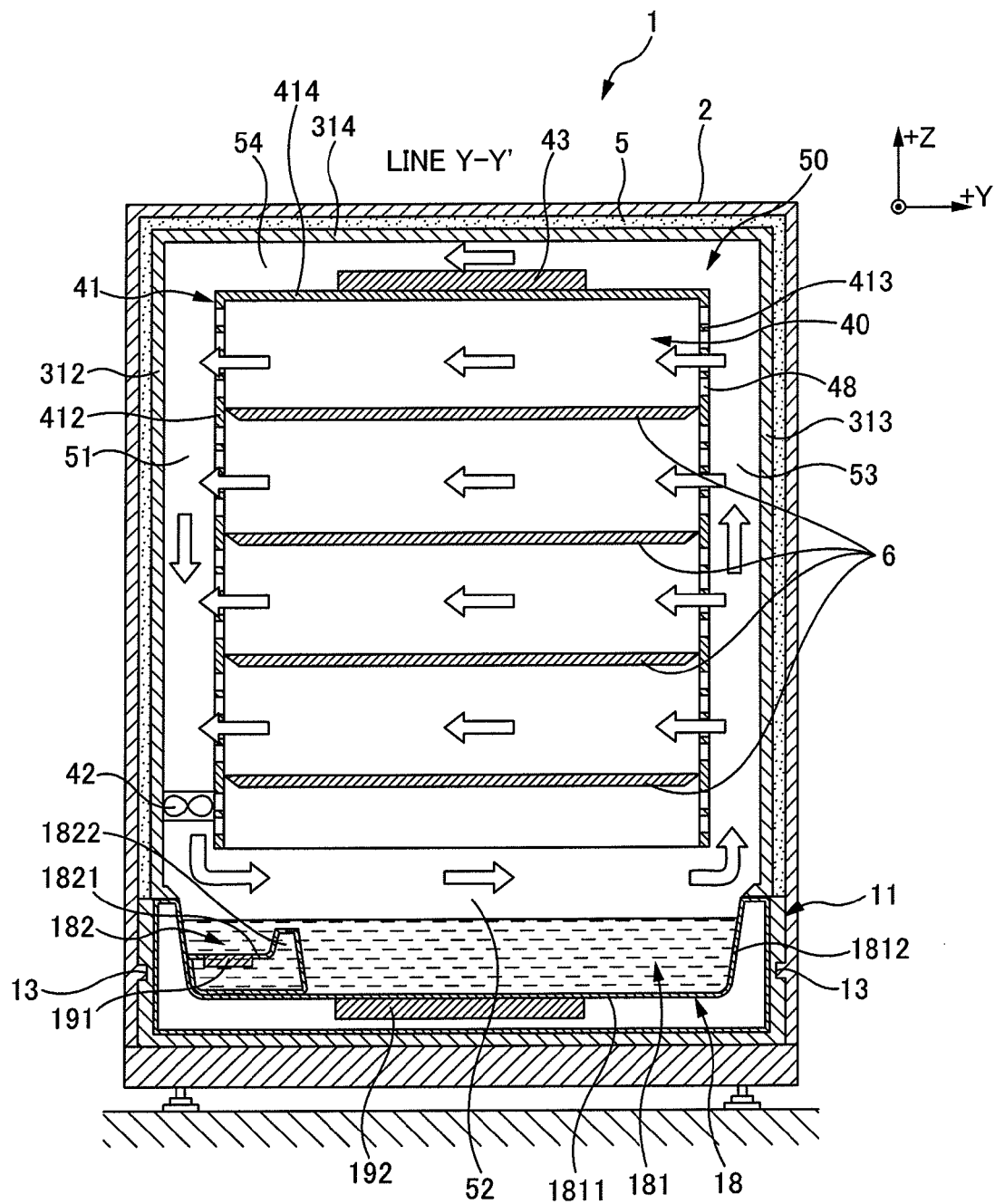
FIG. 6 is a diagram illustrating an operation of an incubator 1 when humidification is performed in an inner box 3.

FIG. 6 is a cross-sectional view of the incubator 1 along a line Y-Y' of FIG. 2 and also is a diagram illustrating an operation of the incubator 1 when the humidification is performed in the inner box 3. The operation illustrated in the drawing is performed when the humidity inside the culture chamber 40 is lower than an appropriate value (target value), for example.

When the humidification is performed in the inner box 3, firstly, a necessary amount of water is to be supplied beforehand to the first containing unit 181 of the dish structure 18. The user can conveniently supply water to the first containing unit 181 by pulling out the drawer 11. The user can easily check the remaining amount of the water retained in the first containing unit 181 by pulling out the drawer 11.

As illustrated in FIG. 6, when the humidification is performed in the inner box 3, the fan 42 is rotated to circulate the air. As indicated by an arrow in the drawing, this air current causes the air to continuously flow from the first clearance space 51 into the second clearance space 52, and the air flowing into the second clearance space 52 gets in contact with the water retained in the first containing unit 181. The air moisturized by getting in contact with the water is pressed by the air subsequently flowing from the first clearance space 51, thereby flowing into the third clearance space 53.

As described above, a large number of air holes 48 are formed on the face of the sideboard 413. For this reason, a portion of the air flowing into the third clearance space 53 flows upward in the third clearance space 53 toward the fourth clearance space 53, while other portion of the air flowing therein flows into the culture chamber 40 through the air holes 48 formed on the sideboard 413. Here, in the first clearance space 51, a downward current is generated by an operation of the fan 42, and thus the first clearance space 51 has a negative pressure as compared with the third clearance space 52. Therefore, the air in the third clearance space 53 is efficiently taken into the culture chamber 40 thereby generating an air current (air current in the +Y→–Y direction) in the culture chamber 40, and such an air is discharged to the first clearance space 51 thereby joining the downward current flowing in the first clearance space 51.

As such, with the incubator 1 according to an embodiment of the present invention, when the humidification is performed, the water is efficiently supplied to the air circulating in the duct 50 as well as the moisturized air containing a moisture content can efficiently be sent into the culture chamber 40, thereby being able to efficiently control the humidity in the culture chamber 40.

<Operation when Rapid Humidification is Performed>

Figure 7:
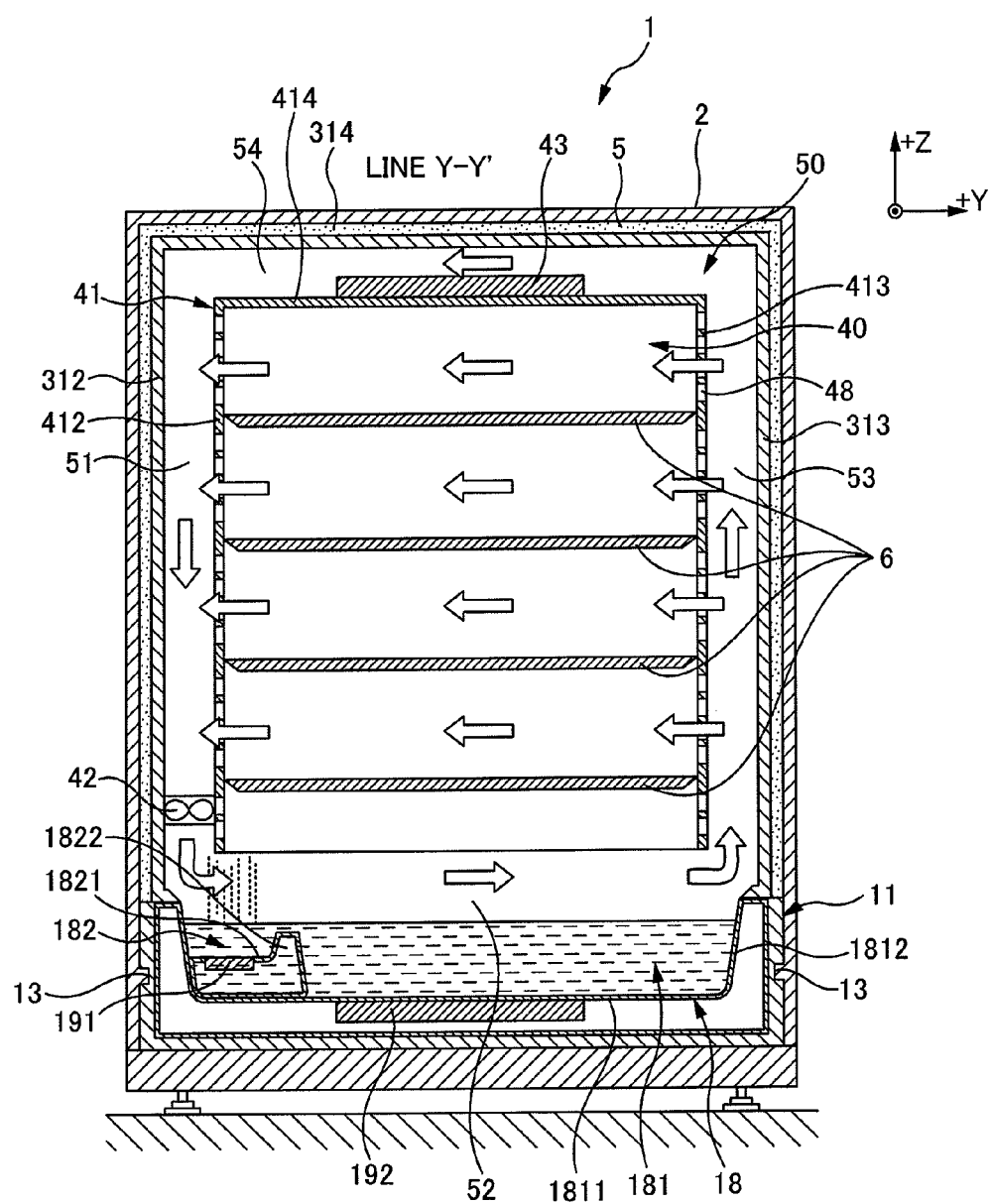
FIG. 7 is a diagram illustrating an operation of an incubator 1 when rapid humidification is performed in an inner box 3.

FIG. 7 is, similarly to FIG. 3, a cross-sectional view of the incubator 1 along the line Y-Y' of FIG. 2 and is a diagram illustrating an operation of the incubator 1 when rapid humidification is performed in the inner box 3. The rapid humidification operation is performed when the humidity inside the culture chamber 40 is lower than the appropriate value (target value) and the rapid humidification in the inner box 3 is desired. This is, for example, a case where the humidity inside is lowered by the opening and closing of the door.

When rapid humidification is performed in the inner box 3 in the same manner as in the case of the humidification described above, the water is supplied beforehand to the first containing unit 181 of the dish structure 18. When the rapid humidification is performed, unlike the case of the humidification, the water is to be supplied to the first containing unit 181 to such an extent that a sufficient amount of water flows in the second containing unit 182. That is to say, when the humidification is performed, the water is supplied to both of the first containing unit 181 and the second containing unit 182. When the water level sensor detects that the water level of the second containing unit 182 has dropped to a predetermined water level, the ultrasonic vibrator 191 stops operating so as not to operate with no water therein.

Similarly to the case where the humidification is performed, when the rapid humidification is performed, the fan 42 is rotated to circulate the air in the duct 50 and the culture chamber 40. Additionally, the ultrasonic vibrator 191 is operated when the rapid humidification is performed. When the ultrasonic vibrator 191 is operated, the water retained in the second containing unit 182 is atomized (turned into mist) to form a water column at a water surface of the second containing unit 182, and the air flowing in the second clearance space 52 gets in contact with water drops (mist) of the water column.

Thus, since the incubator 1 according to an embodiment of the present invention includes a structure in which the air circulating in the duct 50 and the water atomized by the ultrasonic vibrator 191 are brought into contact with each other (gas-liquid contact structure), thereby increasing an area of contact between the air flowing in the second clearance space 52 and the water, so that moisture can be supplied efficiently and positively to the air flowing in the second clearance space 52. This makes it possible to efficiently send the moisturized air containing the water to the culture chamber 40, thereby being able to efficiently perform the humidity control inside the culture chamber 40.

<Operation when Sterilization Processing is Performed>

Figure 8:
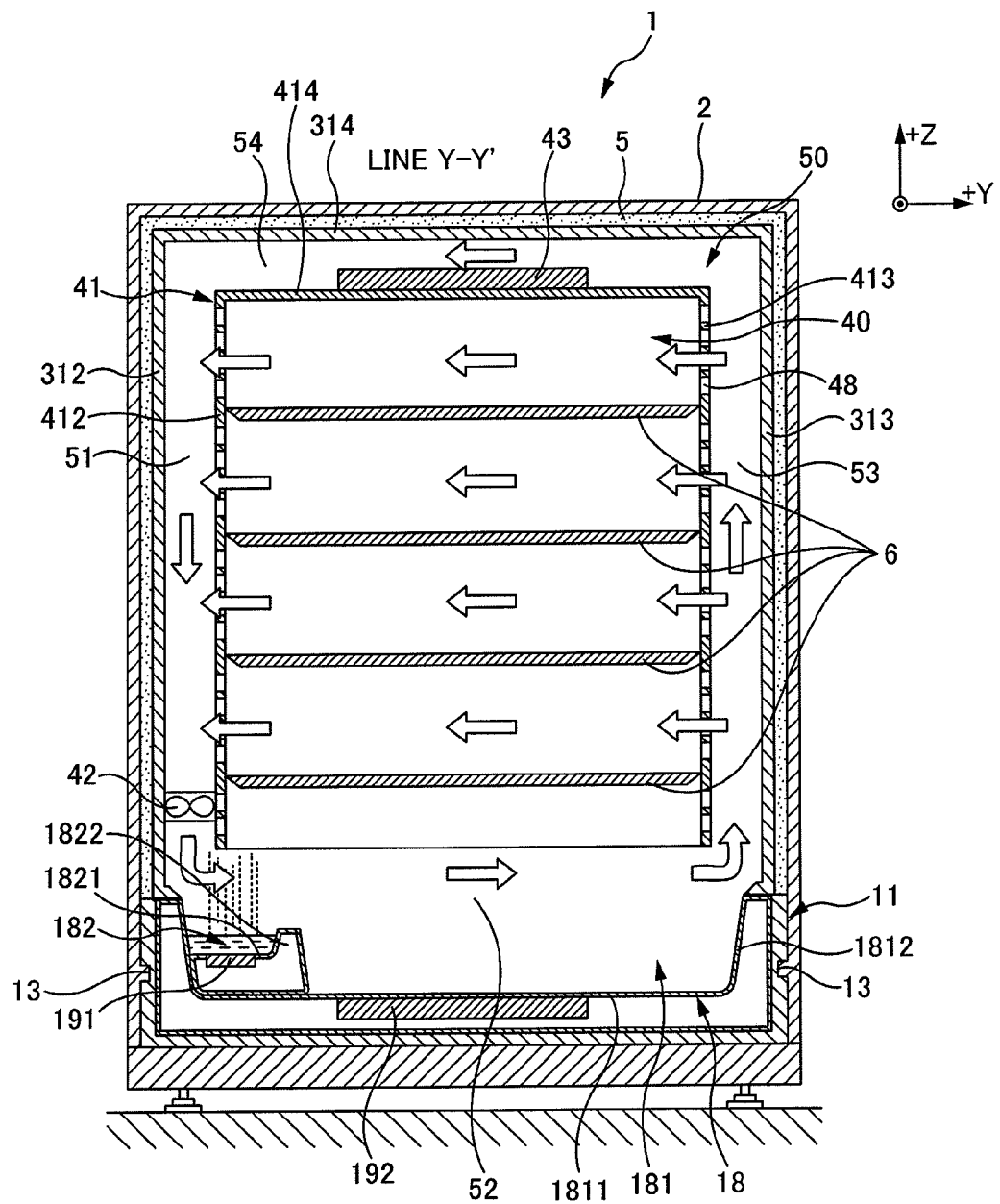
FIG. 8 is a diagram illustrating an operation of an incubator 1 when sterilization processing is performed in an inner box 3.

FIG. 8 is, similarly to FIG. 3, a cross-sectional view of the incubator 1 along the line Y-Y' of FIG. 2, and is a diagram illustrating an operation of the incubator 1 when sterilization processing is performed in the inner box 3.

As illustrated in the drawing, when the sterilization processing is performed, a processing liquid for sterilization such as an aqueous solution of hydrogen peroxide is retained in the second containing unit 182 of the dish structure 18. The user can conveniently supply the processing liquid for sterilization to the second containing unit 182 by pulling out the drawer 11 from the storage unit 12. If a volume of the second containing unit 182 is determined so as to be equal to an amount required for one time of the sterilization processing, for example, a measuring work can be omitted.

Similarly to the case where the humidification is performed or the case where the rapid humidification is performed, when the sterilization processing is performed, the fan 42 is rotated to circulate the air in the duct 50 and the culture chamber 40. Similarly to the case where the rapid humidification is performed, the ultrasonic vibrator 191 is operated to positively bring the processing liquid for sterilization retained in the second containing unit 182 into contact with the air flowing in the second clearance space 51.

Similarly to the case where the rapid humidification is performed, a water column of the processing liquid for sterilization is formed by the ultrasonic vibrator 191, thereby increasing the area of contact between the air flowing in the second clearance space 52 and the processing liquid for sterilization, which makes it possible to efficiently supply the processing liquid for sterilization to the air flowing in the second clearance space 52.

As such, with the incubator 1 according to an embodiment of the present invention, when the rapid humidification is performed, the processing liquid for sterilization can be supplied efficiently and positively to the air circulating inside the duct 50 as well as the air containing the processing liquid for sterilization can efficiently be sent into the duct 50 and the culture chamber 40, thereby being able to efficiently perform the sterilization securely and efficiently inside the duct 50 and the culture chamber 40.

The incubator 1 according to an embodiment of the present invention is capable of flexibly responding to the need for supply to the incubator 1 of a plurality of types of liquids with required supply quantities different from on another. The same ultrasonic vibrator can be used for the atomization of both a first liquid and a second liquid. Thus, it is unnecessary to provide the ultrasonic vibrator 191 separately for each of the liquids, thereby being able to simplify a configuration and a manufacturing process, and reduce manufacturing costs, etc., in the incubator 1.

In the incubator 1 according to an embodiment of the present invention, either the humidification or the rapid humidification can be selected to perform humidification processing in the culture chamber 40, thereby being able to respond to the user's needs in a flexible manner. Further, power consumption when the incubator 1 is operated can be reduced by not performing unnecessary rapid humidification.

Second Embodiment

Figure 9:
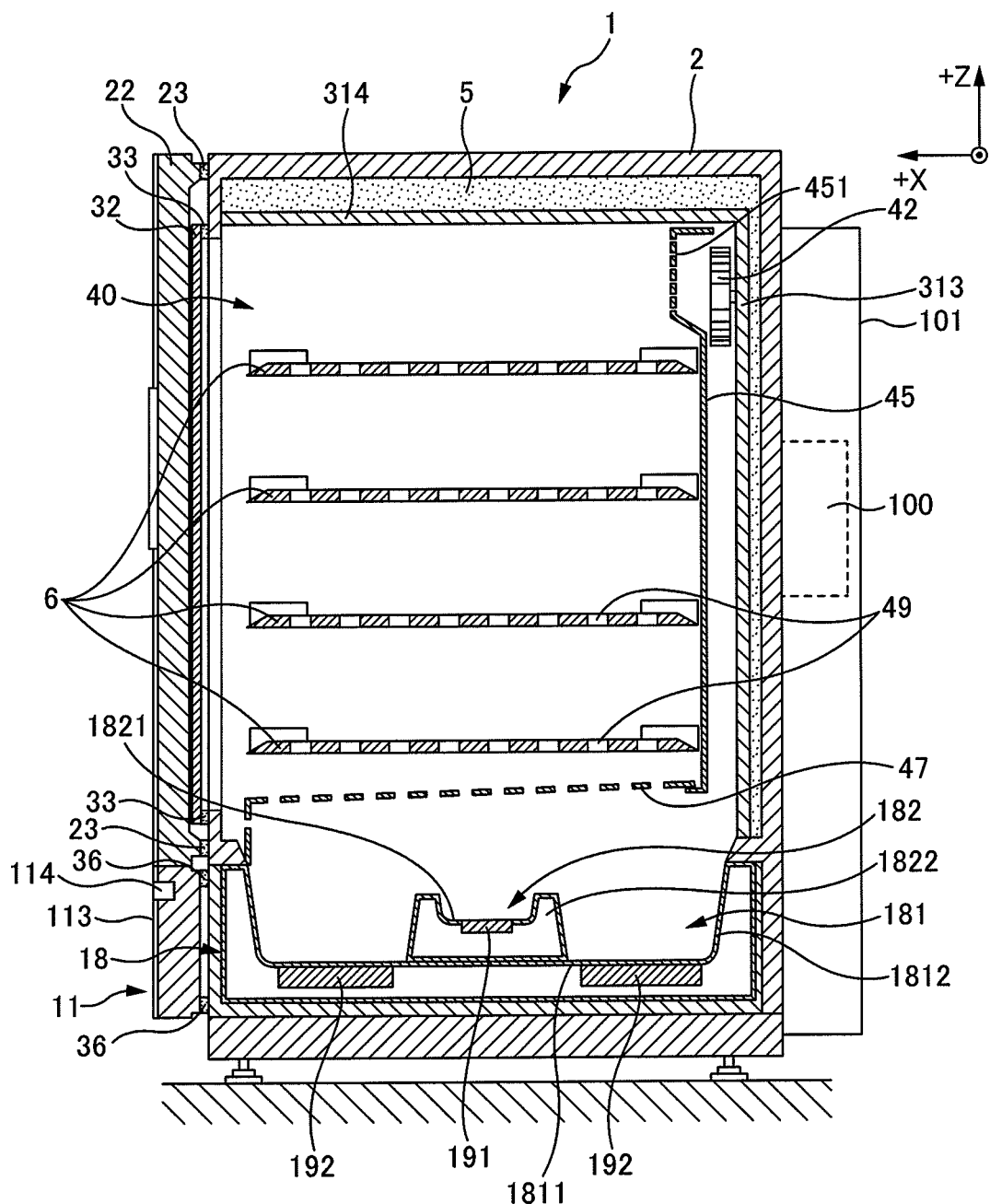
FIG. 9 is a cross-sectional view of an incubator 1 which is to be described as a second embodiment of the present invention.

FIG. 9 is a cross-sectional view of the incubator 1 which is to be described as a second embodiment of the present invention. The incubator 1 according to a second embodiment of the present invention differs from the incubator 1 according to a first embodiment of the present invention in a structure inside the inner box 3 and an air circulation path inside the inner box 3, but is the same as the incubator 1 according to a first embodiment of the present invention in other configurations.

As illustrated in the drawing, the incubator 1 according to a second embodiment of the present invention does not include a configuration corresponding to the case 41 in the incubator 1 according to a first embodiment of the present invention. In the incubator 1 according to a second embodiment of the present invention, a back face board 45 is provided on the back face side (−Y side) of the inner box 3 and is disposed in parallel with the backboard 311 of the inner box 3, extending over the shelf boards 6 as a whole. As illustrated in the drawing, the duct 50 is formed on the back face side in the inner box 3 by this back face board 45.

On the upper (+Z direction) part of the back face board 45, a large number of air holes 451 are formed by the punching process, etc. At the end portion of the upper (+x direction) part of the duct 50, the fan 42 (fan motor, multi-blade fan, etc.) is provided that takes in a gas from the space in which the shelf boards 6 are disposed (hereinafter this space is referred to as the culture chamber 40) through the air holes 451, and sends out the taken-in gas downward inside the duct 50.

The lower end of the back board 411 is distanced from the dish structure 18 by a predetermined space, thereby connecting the duct 50 with the culture chamber 40 below the back face board 45. A cover 47 is provided between the lowermost shelf board 6 and the drawer 11. A large number of air holes 471 are formed on the substantially horizontal face of the cover 47. In the incubator 1 according to a second embodiment of the present invention, the cover 47 is not necessarily an indispensable constituent element. On a face of each of the shelf boards 6, a large number of air holes 49 to allow the air current to pass therethrough in the vertical direction (±Z direction) are formed by the punching process, etc.

<Operation when Humidification is Performed>

Figure 10:
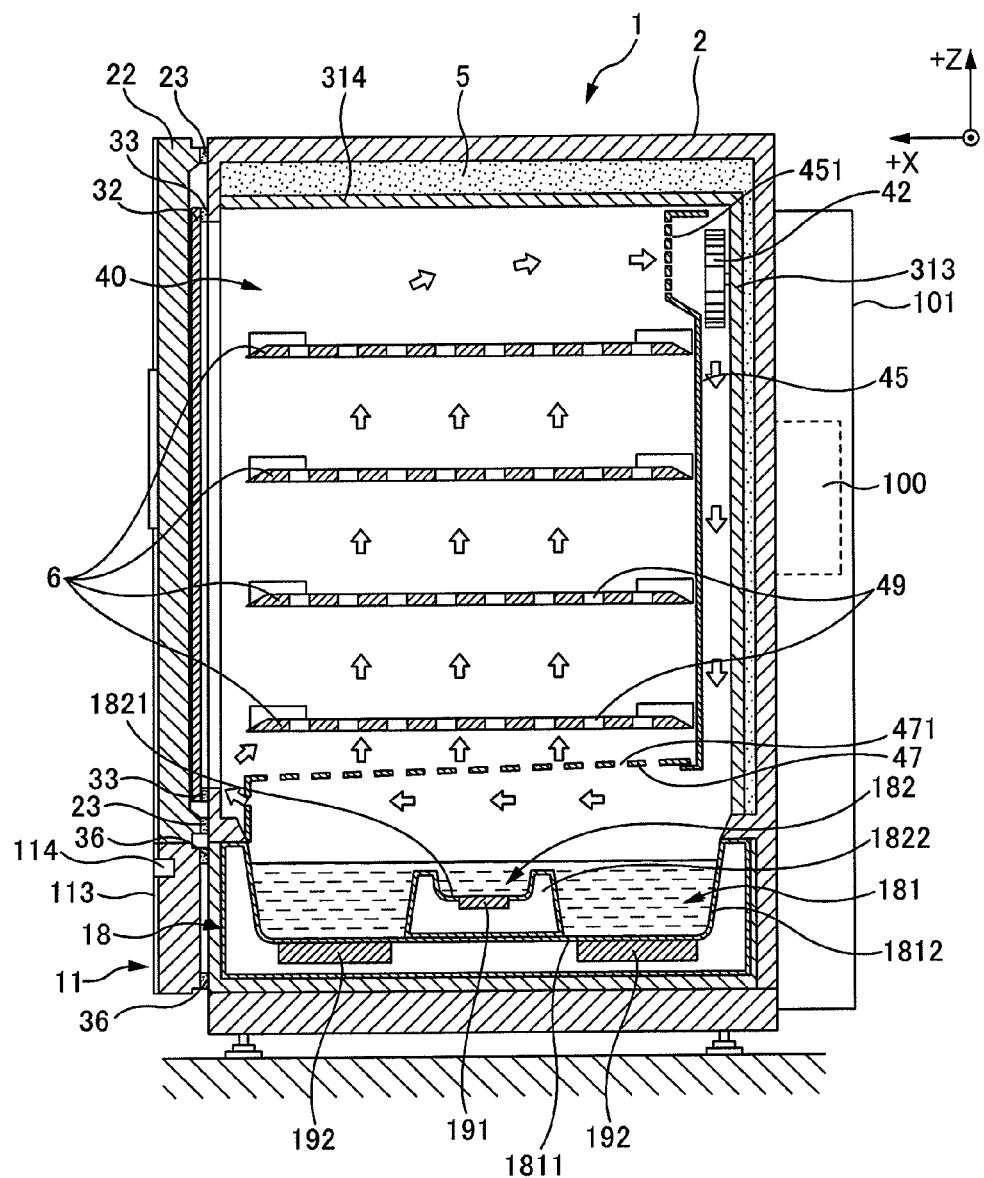
FIG. 10 is a diagram illustrating an operation of an incubator 1 when humidification is performed in an inner box 3, in an incubator 1 which is to be described as a second embodiment of the present invention.

FIG. 10 is a diagram illustrating an operation of the incubator 1 according to a second embodiment of the present invention when humidification is performed. The operation illustrated in the drawing is performed, when the humidity inside the culture chamber 40 is lower than the appropriate value (target value), for example. Similarly to the incubator 1 according to a first embodiment of the present invention, when the humidification is performed in the inner box 3, a necessary amount of water is to be supplied beforehand to the first containing unit 181 of the dish structure 18.

As illustrated in the drawing, when the humidification is performed, the fan 42 is rotated to generate a downward air current in the dust 50. This causes the air of the culture chamber 40 to be taken into the duct 50 from the upper part of the duct 50 and the taken-in air goes downward in the duct 50 to be sent to the lower part of the duct 50.

The air sent to the lower part of the duct 50 flows down from the lower part of the duct 50 toward the liquid surface of the first containing unit 181, and the air flowing down from the duct 50 gets in contact with the water retained in the first containing unit 181. Through contact with the water, the air contains moisture and the air containing the moisture pushed out by the air subsequently flowing down from the duct 50, to be changed into an upward current, thereby flowing into the culture chamber 40 through the air holes 471 of the cover 47. The air flowing into the culture chamber 40 goes upward through the air holes 49 of the shelf boards 6, is sent to the upper part of the inner box 3, and is taken in again through the air holes 451 of the back face board 45 to flow downward.

As such, with the incubator 1 according to an embodiment of the present invention, when the humidification is performed, the moisture is efficiently supplied to the air flowing down from the duct 50 as well as the moisturized air containing the water is efficiently sent into the culture chamber 40, thereby being able to efficiently control the humidity in the culture chamber 40.

Further, with the incubator 1 according to a second embodiment of the present invention, the duct 50 to circulate the gas can be configured only by the back board 411, without the sideboards 412 and 413, the ceiling board 414, etc., being provided as in the incubator 1 according to a first embodiment of the present invention.

<Operation when Rapid Humidification is Performed>

Figure 11:
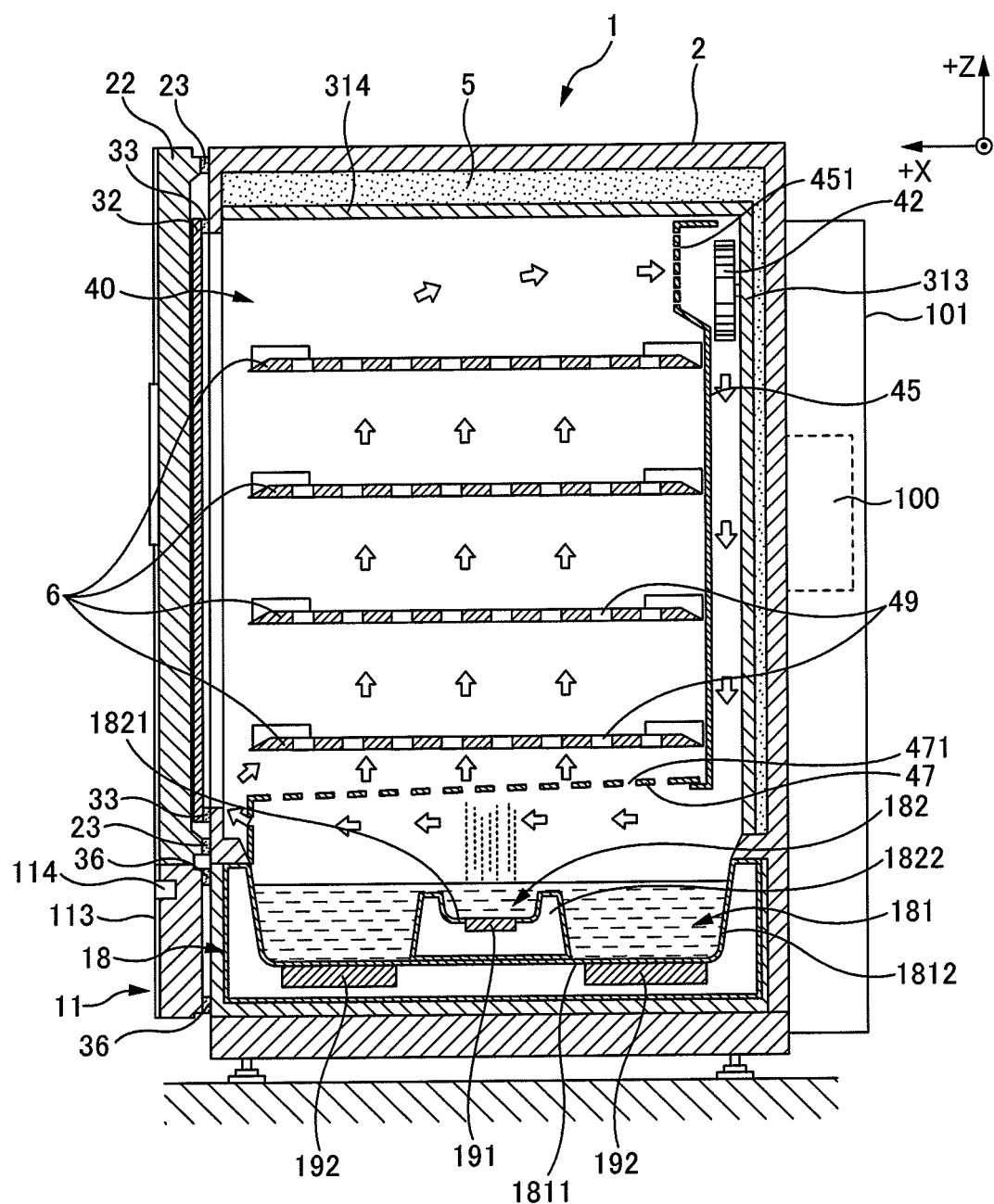
FIG. 11 is a diagram illustrating an operation of an incubator 1 when rapid humidification is performed in an inner box 3, in an incubator 1 which is to be described as a second embodiment of the present invention.

FIG. 11 is a diagram illustrating an operation of the incubator 1 according to a second embodiment of the present invention when the rapid humidification is performed. The operation illustrated in the drawing is performed when the humidity inside the culture chamber 40 is lower than the appropriate value (target value) and the rapid humidification in the inner box 3 is desired, for example.

When the rapid humidification is performed in the inner box 3, similarly to the case of the humidification described above, the water is to be supplied beforehand to the first containing unit 181 of the dish structure 18. When the rapid humidification is performed, unlike the case of the humidification, the water is to be supplied to the first containing unit 181 to such an extent that a sufficient amount of water flows in the second containing unit 182.

Similarly to the case where the humidification is performed, when the rapid humidification is performed, the fan 42 is rotated to circulate the air in the duct 50 and the culture chamber 40. Additionally, the ultrasonic vibrator 191 is operated when the rapid humidification is performed. The ultrasonic vibrator 191 is operated, to form a water column on the water surface of the second containing unit 182, and the air flowing down from the duct 50 gets in contact with water drops (mist) of this water column. Thus, an area of contact between the air flowing down from the duct 50 and the water is increased, thereby being able to efficiently supply moisture to the air flowing down from the duct 50.

As such, with the incubator 1 according to an embodiment of the present invention, when the rapid humidification is performed, moisture is supplied efficiently and positively to the air flowing down from the duct 50. Therefore, the moisturized air containing the water can be efficiently sent to the culture chamber 40, thereby being able to efficiently perform the humidity control inside the culture chamber 40.

<Operation when Sterilization Processing is Performed>

Figure 12:
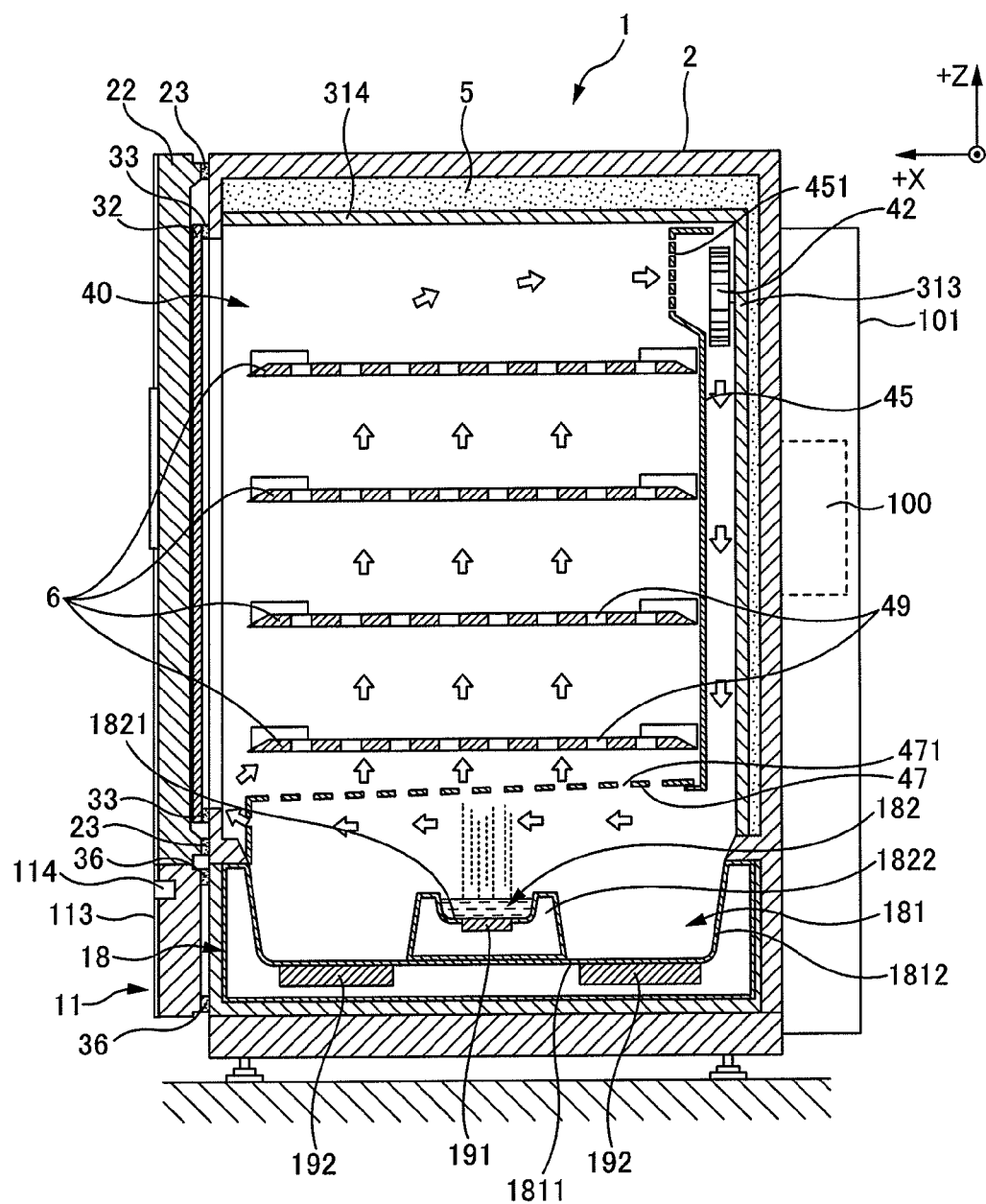
FIG. 12 is a diagram illustrating an operation of an incubator 1 when sterilization processing is performed in an inner box 3, in an incubator 1 which is to be described as a second embodiment of the present invention.

FIG. 12 is a diagram illustrating the operation of the incubator 1 according to a second embodiment of the present invention when the sterilization processing is performed. As illustrated in the drawing, when the sterilization processing is performed, the processing liquid for sterilization such as the aqueous solution of hydrogen peroxide is retained in the second containing unit 182. The user can conveniently supply the processing liquid for sterilization to the second containing unit 182 by pulling out the drawer 11. If a volume of the second containing unit 182 is set so as to be equal to an amount required for one time of the sterilization processing, for example, a measuring work can be omitted.

Similarly to the case where the humidification is performed or the case where the rapid humidification is performed, when the sterilization processing is performed, the fan 42 is rotated to circulate the air in the duct 50 and the culture chamber 40. Similarly to the case where the rapid humidification is performed, the ultrasonic vibrator 191 is operated to positively bring the processing liquid for sterilization retained in the second containing unit 182 into contact with the air flowing down from the duct 50.

Similarly to the case where the rapid humidification is performed, a water column of the processing liquid for sterilization is formed by the ultrasonic vibrator 191, thereby increasing the area of contact between the air flowing down from the duct 50 and the processing liquid for sterilization, which makes it possible to efficiently supply the processing liquid for sterilization to the air flowing down from the duct 50.

As such, with the incubator 1 according to an embodiment of the present invention, when the rapid humidification is performed, the processing liquid for sterilization is supplied efficiently and positively to the air circulating inside the duct 50 as well as the air containing the processing liquid for sterilization is efficiently sent into the duct 50 and the culture chamber 40, thereby being able to efficiently perform the sterilization processing securely and efficiently inside the duct 50 and the culture chamber 40.

The above embodiments of the present invention are simply for facilitating the understanding of the present invention and are not in any way to be construed as limiting the present invention. The present invention may variously be changed or altered without departing from its spirit and encompass equivalents thereof.

For example, in order to prevent contamination inside the culture chamber 40 more securely, the incubator 1 may be provided with an ultraviolet germicidal lamp, an ozone generator, etc.

What is claimed is:

1. An incubator comprising:
a culture chamber configured to accommodate culture;
a dish structure configured to contain a liquid;

an ultrasonic vibrator provided in a part of the dish structure, the ultrasonic vibrator configured to atomize the liquid; and a gas-liquid contact structure configured to bring the atomized liquid into contact with air in the chamber to be cultured, wherein the dish structure includes:

a first containing unit defined by a first bottom face and a first side face disposed around the first bottom face; and a second containing unit provided in the first containing unit, and defined by a second bottom face and a second side face disposed around the second bottom face, the second side face having a height shorter than that of the first side face, and the ultrasonic vibrator is provided on the second bottom face.

2. The incubator of claim 1, wherein water is retained in the first containing unit to maintain humidity inside the culture chamber at a predetermined humidity, and the water or a processing liquid to sterilize an inside of the culture chamber is retained in the second containing unit.

3. The incubator of claim 1, further comprising:

a drawer structure through which the dish structure is pulled out or pushed in the dish structure with respect to the incubator.

4. The incubator of claim 1, wherein the gas-liquid contact structure includes:

a circulating mechanism configured to circulate the air inside the culture chamber; and a mechanism configured to bring the air circulated in the culture chamber by the circulating mechanism into contact with the liquid atomized by the ultrasonic vibrator.

5. The incubator of claim 4, wherein the culture chamber is substantially of a rectangular parallelepiped shape, wherein a plurality of shelf boards, on which the culture is placed, are provided in parallel in the culture chamber, wherein the gas-liquid contact structure further includes a flow path configured to circulate the air along a lower face of the culture chamber, a first side face of the culture chamber, an upper face of the culture chamber, and a second side face opposed to the first side face, wherein the dish structure is arranged so that the air circulating along the lower face of the culture chamber gets in contact with a liquid face of the liquid retained in the dish structure, and wherein the gas-liquid contact structure further includes a flow path configured to cause the air flowing upward along the first side face to flow into a space between the shelf boards adjacent to each other and cause the air flowing out of the space between the shelf boards to join the air flowing downward along the second side face.

6. The incubator of claim 1, wherein the culture chamber is substantially of a rectangular parallelepiped shape, wherein a plurality of shelf boards, on which the culture is placed, are provided in parallel in the culture chamber, wherein, the circulating mechanism includes a flow path configured to cause the air to flow downward along a back face of the culture chamber, wherein the dish structure is arranged below the culture chamber so that the air flowing downward along the back face gets in contact with a liquid face of the liquid retained in the dish structure, and wherein air holes are formed on faces of the shelf boards to guide the air, having got in contact with the liquid, toward an upper part of the culture chamber.

7. The incubator of claim 1, further comprising:

a $CO_2$ gas supply mechanism configured to supply a $CO_2$ gas into the culture chamber;

a $CO_2$ density control mechanism configured to control density of the $CO_2$ gas inside the culture chamber; and a heater configured to heat the air to be supplied into the culture chamber.

* * * * *